United States Patent [19]

Tunstall

[11] 4,279,512
[45] Jul. 21, 1981

[54] METHOD OF MEASUREMENT

[75] Inventor: David F. Tunstall, Redcar, England

[73] Assignee: Tioxide Group Limited, Billingham, England

[21] Appl. No.: 124,331

[22] Filed: Feb. 25, 1980

[30] Foreign Application Priority Data

Mar. 21, 1979 [GB] United Kingdom ............... 09917/79

[51] Int. Cl.$^3$ ............................................. G01N 15/02
[52] U.S. Cl. ..................................... 356/335; 356/409
[58] Field of Search ................... 356/335, 336, 39, 409; 250/573

[56] References Cited

U.S. PATENT DOCUMENTS

| | | | |
|---|---|---|---|
| 3,724,951 | 4/1973 | Seelbinder | 356/336 |
| 4,188,121 | 2/1980 | Hirleman, Jr. et al. | 356/336 |

FOREIGN PATENT DOCUMENTS 749438  4/1969  Belgium .................................. 356/336

Primary Examiner—John K. Corbin
Assistant Examiner—Bruce Y. Arnold
Attorney, Agent, or Firm—Schuyler, Banner, Birch, McKie & Beckett

[57] ABSTRACT

A method of measuring mean particle size and/or standard deviation of particles involves illuminating a suspension of the particles with three beams of radiation of wavelengths $R_1$, $R_2$ and $R_3$ and measuring the beam intensities passing through the suspension. The results are compared with those of the liquid medium free of particles and attenuation ratios of the beams at wavelengths $R_1$ and $R_3$ and at $R_2$ and $R_3$ are compared with previously calculated values for these ratios.

This comparison enables the desired parameters to be obtained easily; preferably by using a spectrophotometer in which two or more optical densities at two or more wavelengths are compared simultaneously.

The method is of particular use for aqueous suspensions of titanium dioxide pigment using wavelengths $R_1$, $R_2$ and $R_3$ of 480 to 520 nanometers, $R_2$ of 600 to 800 nanometers and $R_3$ of 400 to 480 nanometers and not greater than ($R_1$-40) nanometers.

17 Claims, 3 Drawing Figures

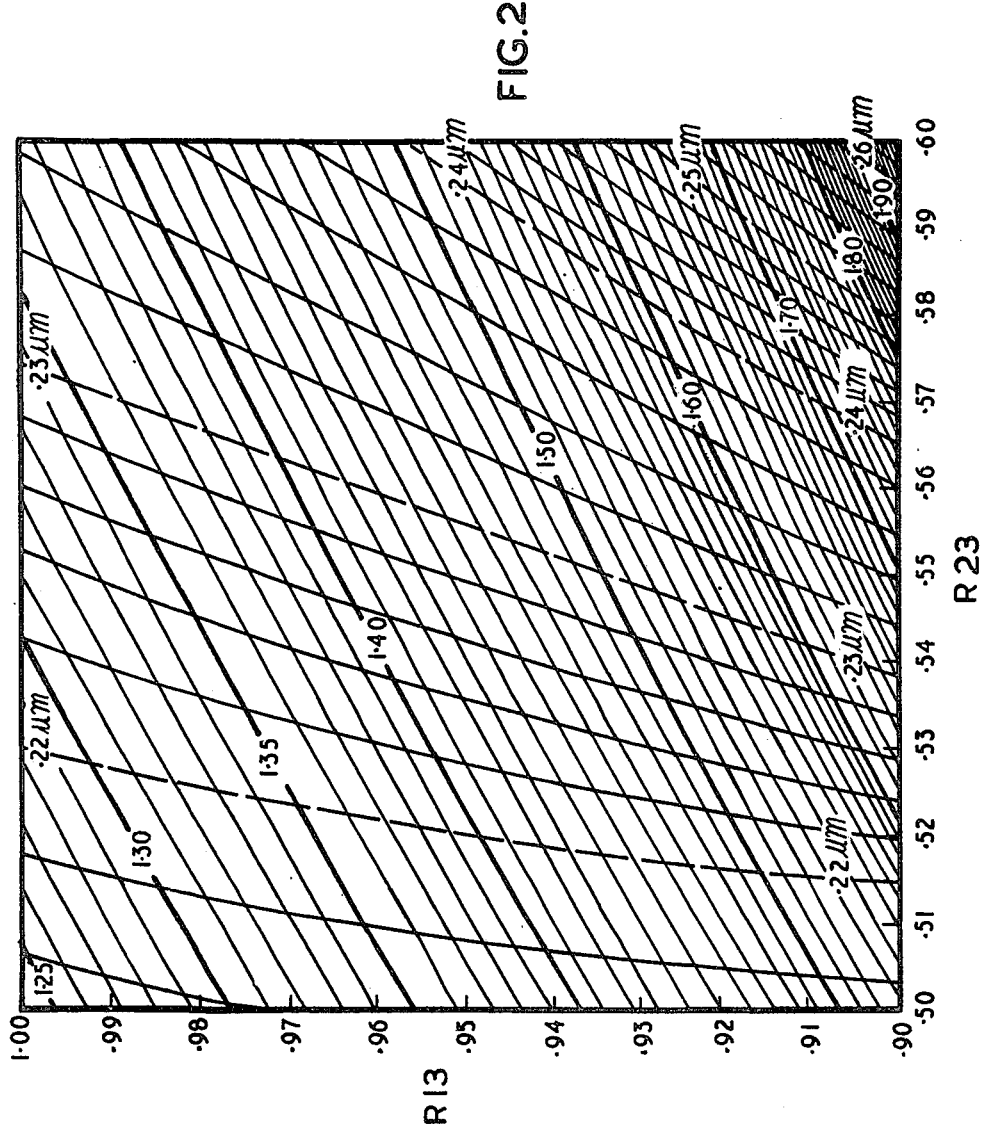

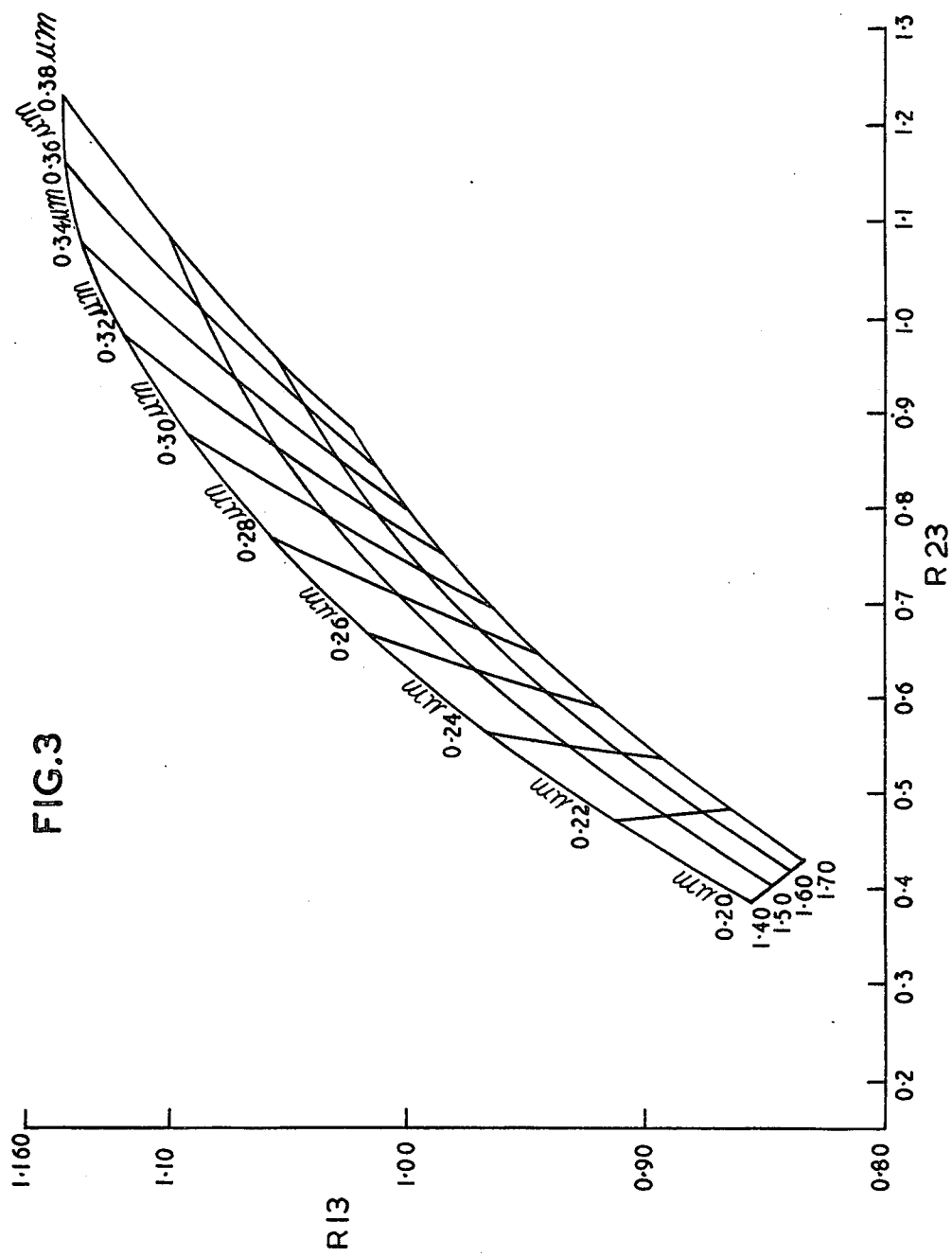

METHOD OF MEASUREMENT

This invention relates to a method of measuring the mean particle size and/or standard deviation of particles.

According to the present invention a method of measuring the mean particle size and/or standard deviation of particles comprises forming a suspension of said particles in a continuous medium wherein the ratio of refractive index of the particles to that of the medium is at least 1.50, illuminating a portion of the suspension with beams of radiation of wavelengths $R_1$, $R_2$ and $R_3$ and measuring the amounts of non-scattered radiation passing through the suspension, illuminating a portion of the continuous medium free of said particles with beams of radiation having respectively wavelengths of $R_1$, $R_2$, and $R_3$ and measuring the amounts of non-scattered radiation passing through the portion of continuous medium for each wavelength, from the measurements so made obtaining the attenuation ratios $R_{13}$ and $R_{23}$ according to the formulae:

$$R_{13} = \frac{\text{Attenuation by particles at wavelength } R_1}{\text{Attenuation by particles at wavelength } R_3}$$

$$R_{23} = \frac{\text{Attenuation by particles at wavelength } R_2}{\text{Attenuation by particles at wavelength } R_3}$$

comparing the so measured attenuation ratios $R_{13}$ and $R_{23}$ with a set of previously calculated values of $R_{13}$ and $R_{23}$ for the particular continuous medium and for a selection of chosen mean particle sizes and/or standard deviations and thereby obtaining the mean particle size and/or standard deviation corresponding to the measured value of $R_{13}$ and $R_{23}$.

According to the invention also a method of measuring the mean particle size and/or standard deviation of particles of titanium dioxide comprises forming a suspension of said particles in a continuous medium wherein the ratio of the refractive index of said particles to that of the medium is at least 1.50, illuminating a portion of the suspension with a beam of radiation of a wavelenth $R_1$ chosen from the range of wavelengths 480 to 520 nanometers and measuring the amount of non-scattered radiation passing through the suspension, illuminating a portion of the suspension with a beam of radiation of wavelength $R_2$ chosen from the range of wavelengths 600 to 800 nanometers and measuring the amount of non-scattered radiation passing through the suspension, illuminating a portion of the suspension with a beam of radiation of a wavelength $R_3$ within the range of wavelengths 400 to 480 nanometers and which is not greater than ($R_1$-40) nanometers and measuring the amount of non-scattered radiation passing through the suspension, illuminating a portion of the continuous medium free of said particles of titanium dioxide with beams of radiation having respectively wavelengths of $R_1$, $R_2$ and $R_3$ nanometers and measuring the amounts of non-scattered radiation passing through the portion of the continuous medium for each wavelength, from the measurements so made obtaining the attenuation ratios $R_{13}$ and $R_{23}$ according to the formulae:

$$R_{13} = \frac{\text{Attenuation by particles at wavelength } R_1}{\text{Attenuation by particles at wavelength } R_3}$$

$$R_{23} = \frac{\text{Attenuation by particles at wavelength } R_2}{\text{Attenuation by particles at wavelength } R_3}$$

comparing the so measured attenuation ratios $R_{13}$ and $R_{23}$ with a set of previously calculated values of $R_{13}$ and $R_{23}$ for the particular continuous medium and for a selection of chosen mean particle sizes and/or standard deviations and hereby obtaining the mean particle size and/or standard deviation corresponding to the measured value of $R_{13}$ and $R_{23}$.

FIG. 2 is an enlarged grid diagram showing a portion of the grid from FIG. 1.

FIG. 3 is a grid diagram similar to FIGS. 1 and 2 for a liquid medium which comprises a solution of a paint resin in an organic solvent (white spirit) having a refractive index of 1.45.

Figure 1:
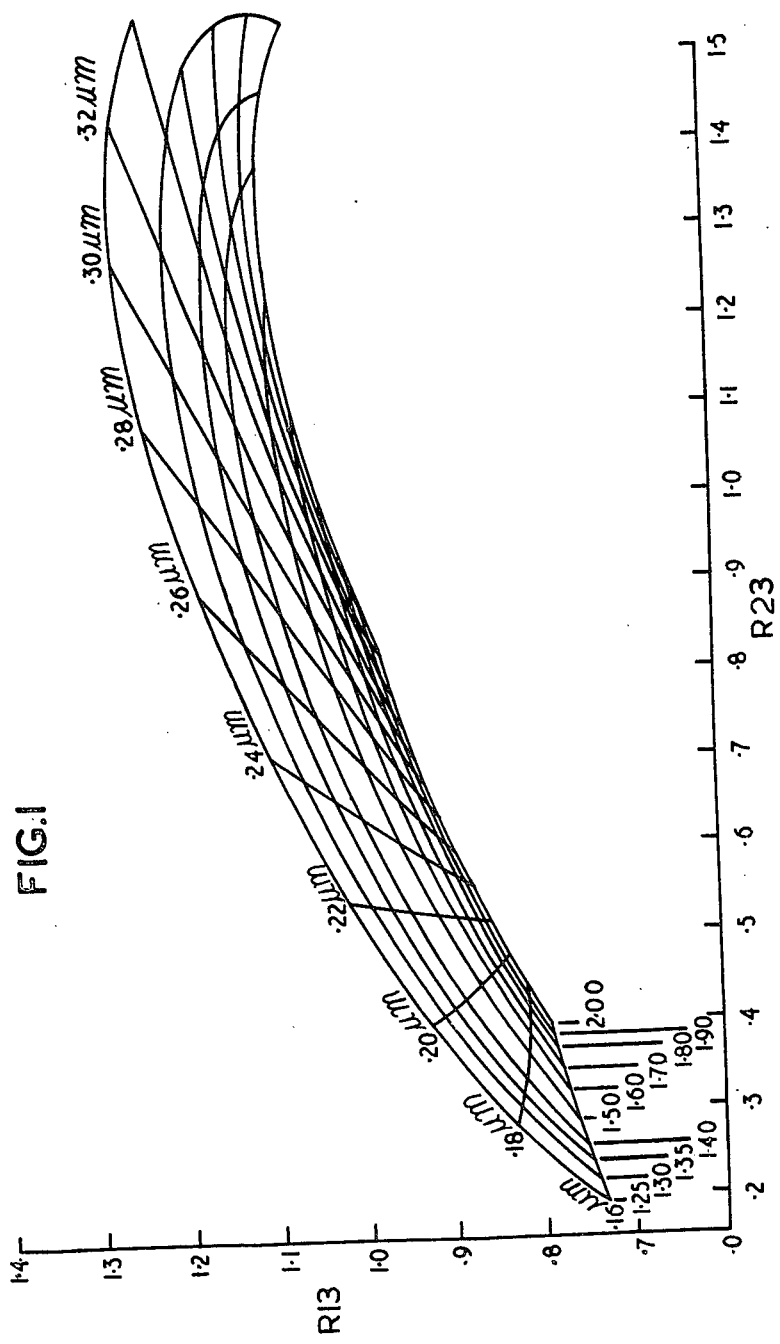
FIG. 1 is a grid diagram showing the ratios of the ratios $R_{13}$ and $R_{23}$ for a series of calculated values of mean particle size of titanium dioxide and for each size range of standard deviations, when the liquid medium is water.

The optical properties of titanium dioxide pigments when incorporated in say, a paint, are largely dependent upon the particle size and the distribution of particle size about the mean for the pigment. During the manufacture of such a pigment it is the usual practice to mill the pigment, often in the form of an aqueous suspension, and it would be advantageous to know the mean particle size and/or its standard deviation at any stage of this milling process, to permit the desired milling conditions to be varied. Similarly during the preparation of a paint, dispersion of the pigment within the resin solution is usually effected by milling and it would be valuable if a method could be devised to permit control of the milling process to obtain a desired mean particle size and/or standard deviation of particle size of the pigment within the paint.

The method described herein makes use of the exceptional electromagnetic radiation scattering properties of non-absorbing particulate materials which have particle diameters of about half the wavelength of the incident radiation.

The present invention provides a method whereby mean particle size and/or standard deviation of pigment designed to scatter white light efficiently may be obtained as a result of measuring the optical density of a suspension of the pigment in a chosen continuous medium.

The method of the invention relies upon the measurement of the optical density of the chosen suspension at three different wavelengths of incident radiation.

One of the chosen wavelengths of radiation referred to herein as $R_1$ usually has a wavelength of 480 to 520 nanometers. A particularly useful and convenient wavelength $R_1$ within this range is 500 nanometers.

Another of the chosen wavelengths referred to herein as $R_2$ and usually is from 600 to 800 nanometers and a particularly useful and convenient wavelength within this range is 700 nanometers.

The third chosen wavelength referred to herein as $R_3$ usually has a value of 400 to 480 nanometers and usually is not greater than ($R_1$-40) nanometers. A particularly useful and convenient wavelength $R_3$ is 440 nanometers.

The optical density of the continuous medium is measured at the chosen wavelengths so that the attenuation of the beam of radiation at each wavelength $R_1$, $R_2$ and $R_3$ due to the presence of the pigment can be calculated.

Two attenuation ratios $R_{13}$ and $R_{23}$ are obtained from the following equations:

$$R_{13} = \frac{\text{Attenuation by pigment at wavelength } R_1}{\text{Attenuation by pigment at wavelength } R_3}$$

$$R_{23} = \frac{\text{Attenuation by pigment at wavelength } R_2}{\text{Attenuation by pigment at wavelength } R_3}$$

These two attenuation ratios $R_{13}$ and $R_{23}$ resulting from the measured optical attenuations at wavelengths $R_1$, $R_2$ and $R_3$ permit the mean size and/or standard deviation to be obtained by comparing the ratio of $R_{13}$ and $R_{23}$ with a calculated set of values of similar ratios for a given set of particle sizes and standard deviations for the particular continuous medium. For any continuous medium it is possible to calculate the attenuation curves for perfect log normal distributions of titanium dioxide particles using so-called Mie equations. The calculated values for one aqueous suspension of the rutile form of titanium dioxide, in which the continuous medium is water with a refractive index of 1.33 are plotted in the form of a grid diagram shown in FIG. 1. From this diagram it will be seen that for any given particle size and standard deviation there are particular values of $R_{13}$ and $R_{23}$. In the case of FIG. 1 the wavelengths have the values $R_1 = 500$ nm, $R_2 = 700$ nm and $R_3 = 440$ nm.

Using a set of calculated values such as these contained in FIG. 1 for a particular continuous medium it is possible, easily and quickly, to obtain from measured values of $R_{13}$ and $R_{23}$ the corresponding mean size and standard deviation of the equivalent log normal distribution. For the majority of practical purposes these values are sufficient to characterise particle size and/or standard deviation of the pigment under examination.

The suspension used in the method of the present invention may be an aqueous suspension, a suspension in any other liquid medium such as a paint resin solution or a suspension in a gas. In order that inaccuracies in the method can be kept within acceptable limits it has been found to be desirable that the concentration of the pigment in the suspension and the length of the path of the beam of radiation within the suspension undergoing test is such that the optical density at wavelength $R_1$ is from 0.5 to 1.5.

By optical density is meant the common logarithm of the ratio of the intensity of the transmitted unscattered radiation to the intensity of the radiation transmitted by the system in the absence of the particulate material. Preferably the conditions are chosen so that the optical density is from 0.95 to 1.05 at the wavelength $R_1$ of the incident radiation. For instance for a suspension of titanium dioxide pigment in water it has been found that an optical density of about unity is obtained for a path length of one centimeter and concentration of 0.05 grammes per liter.

The method is constrained to a particle size range which will normally cover particulate materials designed to scatter electromagnetic radiation. Anatase and rutile, two crystalline forms of titanium dioxide, are the most commonly used materials of this nature, being optimised in particle diameter for scattering and reflection of visible radiation. The method of particle size measurement depends on the material concerned satisfying limiting requirements of two variables, namely the ratio of the mean particle size to the incident radiation wavelength ($R_1$), and the ratio of the refractive index of the particle material to that of the continuous suspending medium.

The mean diameter of the particulate materials should be within a range defined by $d/\lambda = 0.2-1.0$, where d is the mean particle diameter and $\lambda$ is the incident radiation wavelength $R_1$. The refractive index ratio usually should not be less than 1.50.

The portion of suspension is illuminated with radiation having wavelength $R_1$, $R_2$ and $R_3$ and such radiation may be obtained by filtering the unwanted wavelengths from the source of the radiation.

Usually a spectrophotometer is used to measure the optical density of the suspensions and a particularly suitable spectrophotometer is one in which it is possible to measure simultaneously the optical density of a portion of the suspension at one of the chosen wavelengths and the optical density of the liquid medium free of pigment at the chosen wavelength. Thus the attenuation arising from the presence of the pigment at the particular wavelength is easily obtained by difference. Naturally, it is preferred to measure simultaneously two or more optical densities of the suspension at different wavelengths together with the optical density of the liquid medium free of pigment at these wavelengths. In the most preferred method all the necessary measurements of optical density are made simultaneously.

Ideally the optical system used to measure the transmitted radiation intensities should be designed to reduce as much as possible the forward scattered radiation accepted by the detector together with the unscattered transmitted radiation. This effect can give rise to a small degree of variability between results obtained from different spectrometers.

When the two attenuation ratios $R_{13}$ and $R_{23}$ have been obtained these values are compared with a set of previously calculated values for the particular continuous medium and titanium dioxide as described hereinbefore. This set of values, if desired, may be stored within a memory of a computer which, when suitably programmed can produce values for the mean size and for standard deviation corresponding to the measured ratios $R_{13}$ and $R_{23}$. Alternatively the desired mean size and/or standard deviation may be obtained by interpolation from a series of graphs as shown in FIG. 1. FIG. 2 shows parts of FIG. 1 plotted in enlarged form and may be used instead of FIG. 1 to obtain greater accuracy in the results.

FIGS. 1 and 2 represent, as stated hereinbefore, ratios of the ratios $R_{13}$ and $R_{23}$ for a series of calculated values of mean particle size of titanium dioxide and for each size range of standard deviations, when the liquid medium is water. Table 1 below lists the calculated values used to form FIG. 1. FIG. 3 represents a similar set of calculated values when the liquid medium is a solution of a paint resin in an organic solvent (white spirit) having a refractive index of 1.45. Table 2 below lists the calculated values used to form FIG. 3.

The method of the present invention enables control to be exercised over a milling process, e.g. by feedback, during the manufacture of titanium dioxide pigment or during the manufacture of a paint which requires dispersion and milling of this paint within the resin solution forming the basis of this paint. The mean size and/or standard deviation of the pigment at any stage of the milling process can be measured and from the measurements appropriate action taken to obtain the desired mean size and/or standard deviation to produce the desired optical properties of the pigment or paint.

Naturally the method of the invention permits automatic control of the milling process through the use of a computerised control system providing the system has been programmed previously with the values of mean size and/or standard deviation by varying the milling conditions, for example automatically, to obtain these desired values.

The invention is illustrated in the following Example:

EXAMPLE 1

50 gms of a commercially available rutile titanium dioxide pigment were added to a 210 mls screw-capped glass jar containing 60 mls distilled water, 0.1 gm potassium tripolyphosphate and 180 gm 8 MM glass ballotini. The jar was hand shaken to mix the ingredients and then trundled on laboratory rollers for 4 hours. 5 mls of the resulting pigment suspension were diluted to 250 mls with distilled water and then 1 ml of this solution was further diluted by another 250 mls of distilled water to give a final suspension of approximately 0.05 gpl $TiO_2$.

One of a pair of matched 1 cm cells for use on a Beckman DBGT double beam spectrometer was filled with the final $TiO_2$ suspension and the other filled with distilled water. The optical densities of the suspension at 440 nm, 500 nm and 700 nm were measured and found to be 0.944, 1.013 and 0.873. These figures gave ratios $R_{13} = 1.073$, $R_{23} = 0.925$, which in turn (from FIG. 1 or from Table 1) yielded mean diameter 0.31 μm and standard deviation 1.48 for the pigment in suspension.

TABLE I

| Diameter (μm) | Std. Dev. | $R_{13}$ | $R_{23}$ |
|---|---|---|---|
| .16 | 1.25 | 0.730 | 0.193 |
| | 1.30 | 0.740 | 0.216 |
| | 1.35 | 0.744 | 0.235 |
| | 1.40 | 0.751 | 0.253 |
| | 1.50 | 0.764 | 0.286 |
| | 1.60 | 0.772 | 0.319 |
| | 1.70 | 0.778 | 0.344 |
| | 1.80 | 0.784 | 0.364 |
| | 1.90 | 0.788 | 0.379 |
| | 2.00 | 0.791 | 0.393 |
| .18 | 1.25 | 0.832 | 0.279 |
| | 1.30 | 0.826 | 0.297 |
| | 1.35 | 0.824 | 0.314 |
| | 1.40 | 0.821 | 0.329 |
| | 1.50 | 0.818 | 0.358 |
| | 1.60 | 0.816 | 0.381 |
| | 1.70 | 0.818 | 0.399 |
| | 1.80 | 0.816 | 0.413 |
| | 1.90 | 0.815 | 0.424 |
| | 2.00 | 0.815 | 0.434 |
| .20 | 1.25 | 0.926 | 0.393 |
| | 1.30 | 0.912 | 0.401 |
| | 1.35 | 0.900 | 0.412 |
| | 1.40 | 0.887 | 0.419 |
| | 1.50 | 0.869 | 0.434 |
| | 1.60 | 0.857 | 0.446 |
| | 1.70 | 0.850 | 0.455 |
| | 1.80 | 0.844 | 0.462 |
| | 1.90 | 0.840 | 0.469 |
| | 2.00 | 0.837 | 0.474 |
| .28 | 1.25 | 1.238 | 1.078 |
| | 1.30 | 1.174 | 0.991 |
| | 1.35 | 1.124 | 0.918 |
| | 1.40 | 1.086 | 0.863 |
| | 1.50 | 1.026 | 0.778 |
| | 1.60 | 0.985 | 0.722 |
| | 1.70 | 0.956 | 0.683 |
| | 1.80 | 0.935 | 0.657 |
| | 1.90 | 0.919 | 0.637 |
| | 2.00 | 0.907 | 0.623 |
| .30 | 1.25 | 1.267 | 1.262 |
| | 1.30 | 1.202 | 1.144 |
| | 1.35 | 1.152 | 1.049 |
| | 1.40 | 1.116 | 0.978 |
| | 1.50 | 1.051 | 0.862 |
| | 1.60 | 1.006 | 0.788 |
| | 1.70 | 0.975 | 0.737 |
| | 1.80 | 0.952 | 0.702 |
| | 1.90 | 0.935 | 0.676 |
| | 2.00 | 0.921 | 0.657 |
| .32 | 1.25 | 1.265 | 1.421 |
| | 1.30 | 1.208 | 1.279 |
| | 1.35 | 1.165 | 1.167 |
| | 1.40 | 1.131 | 1.082 |
| | 1.50 | 1.070 | 0.943 |
| | 1.60 | 1.025 | 0.851 |
| | 1.70 | 0.992 | 0.789 |
| | 1.80 | 0.968 | 0.746 |
| | 1.90 | 0.949 | 0.714 |
| | 2.00 | 0.934 | 0.690 |
| .22 | 1.25 | 1.016 | 0.533 |
| | 1.30 | 0.992 | 0.528 |
| | 1.35 | 0.969 | 0.524 |
| | 1.40 | 0.948 | 0.521 |
| | 1.50 | 0.916 | 0.516 |
| | 1.60 | 0.896 | 0.514 |
| | 1.70 | 0.881 | 0.512 |
| | 1.80 | 0.870 | 0.512 |
| | 1.90 | 0.863 | 0.512 |
| | 2.00 | 0.857 | 0.513 |
| .24 | 1.25 | 1.102 | 0.701 |
| | 1.30 | 1.065 | 0.672 |
| | 1.35 | 1.031 | 0.650 |
| | 1.40 | 1.003 | 0.631 |
| | 1.50 | 0.959 | 0.602 |
| | 1.60 | 0.930 | 0.583 |
| | 1.70 | 0.908 | 0.570 |
| | 1.80 | 0.894 | 0.561 |
| | 1.90 | 0.884 | 0.555 |
| | 2.00 | 0.876 | 0.551 |
| .26 | 1.25 | 1.179 | 0.885 |
| | 1.30 | 1.127 | 0.830 |
| | 1.35 | 1.085 | 0.784 |
| | 1.40 | 1.049 | 0.746 |
| | 1.50 | 0.996 | 0.691 |
| | 1.60 | 0.960 | 0.653 |
| | 1.70 | 0.934 | 0.627 |
| | 1.80 | 0.916 | 0.610 |
| | 1.90 | 0.902 | 0.597 |
| | 2.00 | 0.892 | 0.587 |
| .34 | 1.25 | 1.234 | 1.537 |
| | 1.30 | 1.197 | 1.389 |
| | 1.35 | 1.163 | 1.264 |
| | 1.40 | 1.138 | 1.173 |
| | 1.50 | 1.083 | 1.015 |
| | 1.60 | 1.039 | 0.910 |
| | 1.70 | 1.006 | 0.838 |
| | 1.80 | 0.981 | 0.789 |
| | 1.90 | 0.961 | 0.749 |
| | 2.00 | 0.945 | 0.721 |
| .36 | 1.25 | | |
| | 1.30 | 1.179 | 1.485 |
| | 1.35 | 1.159 | 1.356 |
| | 1.40 | 1.136 | 1.247 |
| | 1.50 | 1.091 | 1.081 |
| | 1.60 | 1.051 | 0.966 |
| | 1.70 | 1.019 | 0.885 |
| | 1.80 | 0.993 | 0.827 |
| | 1.90 | 0.972 | 0.784 |
| | 2.00 | 0.956 | 0.751 |
| .38 | 1.25 | | |
| | 1.30 | 1.143 | 1.529 |
| | 1.35 | 1.140 | 1.410 |
| | 1.40 | 1.128 | 1.305 |
| | 1.50 | 1.095 | 1.137 |
| | 1.60 | 1.060 | 1.015 |
| | 1.70 | 1.029 | 0.928 |
| | 1.80 | 1.003 | 0.864 |
| | 1.90 | 0.982 | 0.816 |
| | 2.00 | 0.965 | 0.780 |
| .40 | 1.25 | | |

TABLE I-continued

| Diameter (μm) | Std. Dev. | $R_{13}$ | $R_{23}$ |
|---|---|---|---|
| | 1.30 | 1.105 | 1.541 |
| | 1.35 | 1.116 | 1.441 |
| | 1.40 | 1.116 | 1.347 |
| | 1.50 | 1.096 | 1.184 |
| | 1.60 | 1.066 | 1.060 |
| | 1.70 | 1.013 | 0.967 |
| | 1.80 | 1.01 | 0.899 |
| | 1.90 | 0.992 | 0.847 |
| | 2.00 | 0.974 | 0.807 |
| .42 | 1.25 | | |
| | 1.30 | 1.068 | 1.530 |
| | 1.35 | 1.092 | 1.453 |
| | 1.40 | 1.101 | 1.373 |
| | 1.50 | 1.093 | 1.222 |
| | 1.60 | 1.070 | 1.099 |
| | 1.70 | 1.045 | 1.004 |
| | 1.80 | 1.021 | 0.932 |
| | 1.90 | 1.000 | 0.877 |
| | 2.00 | 0.982 | 0.834 |

TABLE II

| Diameter (μm) | Std. Dev. | $R_{13}$ | $R_{23}$ |
|---|---|---|---|
| .20 | 1.40 | 0.856 | 0.386 |
| | 1.50 | 0.846 | 0.404 |
| | 1.60 | 0.838 | 0.419 |
| | 1.70 | 0.833 | 0.430 |
| .22 | 1.40 | 0.914 | 0.473 |
| | 1.50 | 0.891 | 0.477 |
| | 1.60 | 0.876 | 0.480 |
| | 1.70 | 0.865 | 0.483 |
| .24 | 1.40 | 0.268 | 0.567 |
| | 1.50 | 0.934 | 0.554 |
| | 1.60 | 0.910 | 0.544 |
| | 1.70 | 0.893 | 0.536 |
| .26 | 1.40 | 1.016 | 0.668 |
| | 1.50 | 0.972 | 0.634 |
| | 1.60 | 0.941 | 0.608 |
| | 1.70 | 0.918 | 0.590 |
| .28 | 1.40 | 1.058 | 0.772 |
| | 1.50 | 1.005 | 0.713 |
| | 1.60 | 0.968 | 0.671 |
| | 1.70 | 0.941 | 0.643 |
| .30 | 1.40 | 1.092 | 0.877 |
| | 1.50 | 1.033 | 0.792 |
| | 1.60 | 0.991 | 0.735 |
| | 1.70 | 0.962 | 0.695 |
| .32 | 1.40 | 1.117 | 0.978 |
| | 1.50 | 1.056 | 0.869 |
| | 1.60 | 1.012 | 0.796 |
| | 1.70 | 0.981 | 0.745 |
| .34 | 1.40 | 1.134 | 1.072 |
| | 1.50 | 1.074 | 0.942 |
| | 1.60 | 1.030 | 0.855 |
| | 1.70 | 0.997 | 0.794 |
| .36 | 1.40 | 1.141 | 1.156 |
| | 1.50 | 1.086 | 1.010 |
| | 1.60 | 1.044 | 0.911 |
| | 1.70 | 1.011 | 0.840 |
| .38 | 1.40 | 1.142 | 1.228 |
| | 1.50 | 1.096 | 1.072 |
| | 1.60 | 1.056 | 0.962 |
| | 1.70 | 1.023 | 0.884 |

What is claimed is:

1. A method of measuring the mean particle size and/or standard deviation of particles which comprises forming a suspension of said particles in a continuous medium wherein the ratio of refractive index of the particles to that of the medium is at least 1.50, illuminating a portion of the suspension with beams of radiation of wavelengths $R_1$, $R_2$ and $R_3$ and measuring the amounts of non-scattered radiation passing through the suspension, illuminating a portion of the continuous medium free of said particles with beams of radiation having respectively wavelengths of $R_1$, $R_2$ and $R_3$ and measuring the amounts of non-scattered radiation passing through the portion of continuous medium for each wavelength, from the measurements so made obtaining the attenuation ratios $R_{13}$ and $R_{23}$ according to the formulae:

$$R_{13} = \frac{\text{Attenuation by particles at wavelength } R_1}{\text{Attenuation by particles at wavelength } R_3}$$

$$R_{23} = \frac{\text{Attenuation by particles at wavelength } R_2}{\text{Attenuation by particles at wavelength } R_3}$$

comparing the so measured attenuation ratios $R_{13}$ and $R_{23}$ with a set of previously calculated values of $R_{13}$ and $R_{23}$ for the particular continuous medium and for a selection of chosen mean particle sizes and/or standard deviations and thereby obtaining the mean particle size and/or standard deviation corresponding to the measured value of $R_{13}$ and $R_{23}$.

2. A method according to claim 1 in which $R_1$ has a value of from 480 to 520 nanometers.

3. A method according to claim 2 in which $R_1$ has a value of 500 nanometers.

4. A method according to claim 1 in which $R_2$ has a value of from 600 to 800 nanometers.

5. A method according to claim 4 in which $R_2$ has a value of 700 nanometers.

6. A method according to claim 1 in which $R_3$ has a value of from 400 to 480 nanometers and is not greater than ($R_1$-40) nanometers.

7. A method according to claim 6 in which $R_3$ has a value of 440 nanometers.

8. A method according to claim 1 in which the concentration of the particles in the suspension and the length of the path of the beam of radiation within the suspension is such that the optical density at wavelength $R_1$ is from 0.5 to 1.5.

9. A method according to claim 8 in which the optical density is from 0.95 to 1.05.

10. A method according to claim 1 in which the mean diameter of the particulate material is within the range defined by $d/\lambda=0.2$ to $d/\lambda=1.0$ where d is the mean particle diameter and $\lambda$ is the wavelength of the incident radiation $R_1$.

11. A method according to claim 1 in which the beams of radiation of wavelengths $R_1$, $R_2$ and $R_3$ are obtained by filtering unwanted wavelengths from the radiation emitted by a suitable source.

12. A method according to claim 1 in which a spectrophotometer is used to measure the optical density of the suspensions simultaneously at one of the chosen wavelengths $R_1$, $R_2$ or $R_3$ and the optical density of the continuous medium free of said particles at the chosen wavelength.

13. A method according to claim 12 in which two or more optical densities of the suspension at two or more chosen wavelengths $R_1$, $R_2$ or $R_3$ are measured simultaneously with the optical density of the continuous medium free of said particles at the particular wavelengths chosen.

14. A method of measuring the mean particle size and/or standard deviation of particles of titanium dioxide which comprises: forming a suspension of said particles in a continuous medium wherein the ratio of the refractive index of said particles to that of the medium is at least 1.50, illuminating a portion of the suspension with a beam of radiation of a wavelength $R_1$ chosen from the range of wavelengths 480 to 520 nanometers and measuring the amount of non-scattered radiation passing through the suspension, illuminating a portion of the suspension with a beam of radiation of wavelength $R_2$ chosen from the range of wavelengths 600 to 800 nanometers and measuring the amount of non-scattered radiation passing through the suspension, illuminating a portion of the suspension with a beam of radiation of a wavelength $R_3$ within the range of wavelengths 400 to 480 nanometers and which is not greater than ($R_1$-40) nanometers and measuring the amount of non-scattered radiation passing through the suspension, illuminating a portion of the continuous medium free of said particles of titanium dioxide with beams of radiation having respectively wavelengths of $R_1$, $R_2$ and $R_3$ nanometers and measuring the amounts of non-scattered radiation passing through the portion of the continuous medium for each wavelength, from the measurements so made obtaining the attenuation ratios $R_{13}$ and $R_{23}$ according to the formulae:

$$R_{13} = \frac{\text{Attenuation by particles at wavelength } R_1}{\text{Attenuation by particles at wavelength } R_3}$$

$$R_{23} = \frac{\text{Attenuation by particles at wavelength } R_2}{\text{Attenuation by particles at wavelength } R_3}$$

comparing the so measured attenuation ratios $R_{13}$ and $R_{23}$ with a set of previously calculated values of $R_{13}$ and $R_{23}$ for the particular continuous medium and for a selection of chosen mean particle sizes and/or standard deviations and thereby obtaining the mean particle size and/or standard deviation corresponding to the measured value of $R_{13}$ and $R_{23}$.

15. A method according to claim 14 in which the continuous medium is water.

16. A method according to claim 14 in which the optical density of the pigment in the continuous medium is about 1.

17. A method according to claim 16 in which the path length of the beam of radiation through said suspension is about 1 cm and the concentration of said particles in said suspension is about 0.05 grams per liter.

* * * * *